United States Patent
Richmond

(10) Patent No.: US 6,485,472 B1
(45) Date of Patent: *Nov. 26, 2002

(54) SPIKELESS CONNECTION AND DRIP CHAMBER WITH VALVE

(76) Inventor: Frank M. Richmond, 205 A Grant St., Harvard, IL (US) 60033

( * ) Notice: Subject to any disclaimer, the term of this patent is extended or adjusted under 35 U.S.C. 154(b) by 129 days.

This patent is subject to a terminal disclaimer.

(21) Appl. No.: 09/621,181

(22) Filed: Jul. 21, 2000

Related U.S. Application Data

(63) Continuation of application No. 09/041,566, filed on Mar. 12, 1998, now Pat. No. 6,206,860.

(51) Int. Cl.[7] ................................................. A61M 5/00
(52) U.S. Cl. ...................................................... 604/246
(58) Field of Search ............................... 604/30, 89, 91, 604/33, 246–248, 249, 251, 254, 256, 411, 414

(56) References Cited

U.S. PATENT DOCUMENTS

| | | | | |
|---|---|---|---|---|
| 5,405,333 A | * | 4/1995 | Richmond | ................. 604/257 |
| 5,445,623 A | * | 8/1995 | Richmond | ................. 604/251 |
| 5,645,538 A | * | 7/1997 | Richmond | ................. 604/256 |
| 5,735,826 A | * | 4/1998 | Richmond | ................. 604/251 |
| 5,848,994 A | * | 12/1998 | Richmond | ................. 604/248 |
| 6,206,860 B1 | * | 3/2001 | Richmond | ................. 604/246 |

* cited by examiner

*Primary Examiner*—Sharon Kennedy
(74) *Attorney, Agent, or Firm*—Fitch, Even, Tabin, & Flannery

(57) ABSTRACT

A drip chamber includes an elongated transparent container, and a cap. The container has open proximal and distal ends. The cap covers the distal end and further includes a drip forming tube, a cannula and an attachment element used to removably attach the chamber to a connector. The cannula extends distally away from the chamber and is surrounded by the attachment element. A pathway for fluid is established through the cannula and into the chamber.

35 Claims, 6 Drawing Sheets

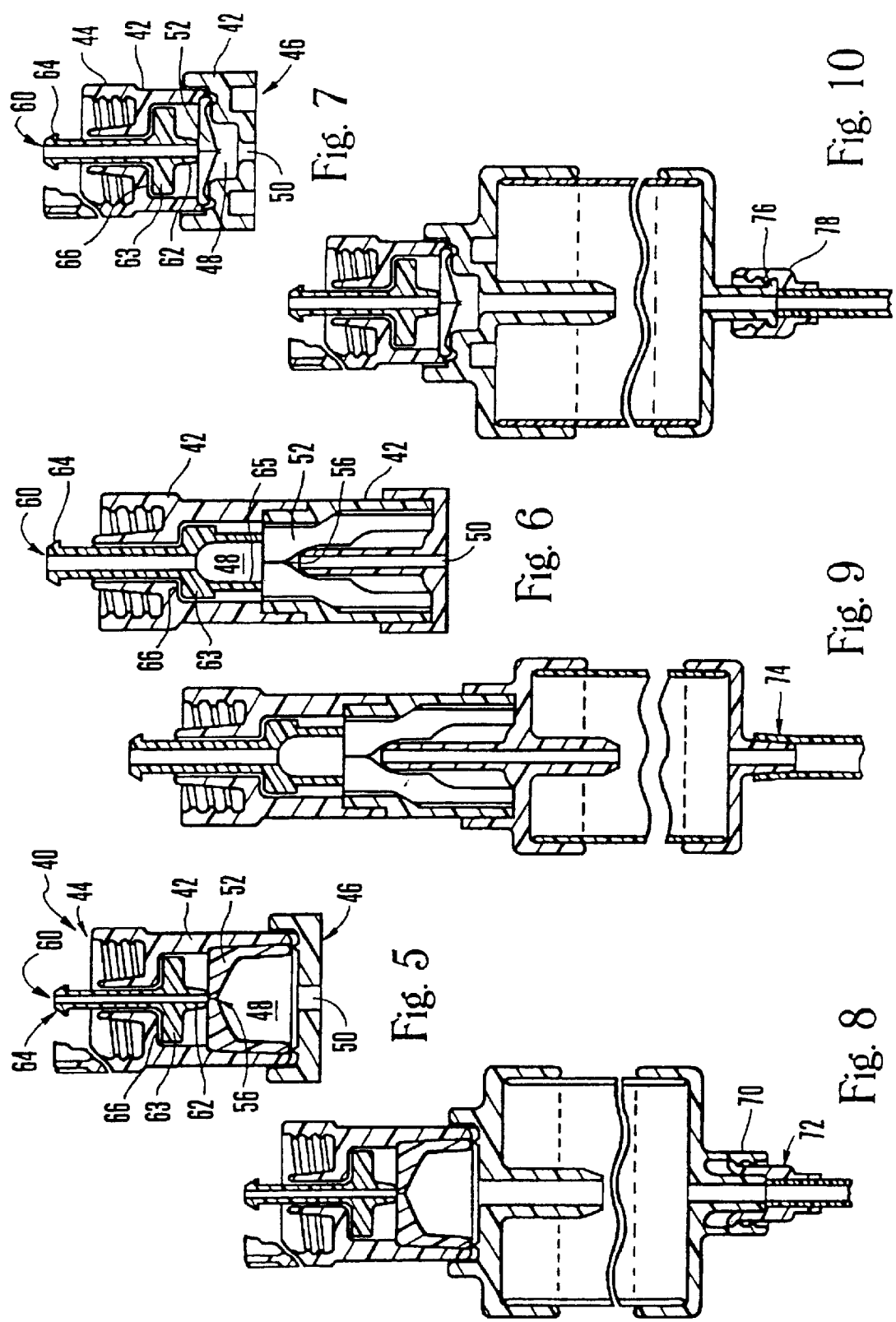

6,485,472 B1

SPIKELESS CONNECTION AND DRIP CHAMBER WITH VALVE

RELATED APPLICATION

This is a continuation, of prior application Ser. No. 09/041,566, filed Mar. 12, 1998, now U.S. Pat. No. 6,206,860, issued Mar. 27, 2001, which is hereby incorporated herein by reference in its entirety.

The present application is a Continuation-In-Part of and claims priority from the following co-pending U.S. Pat. applications:

U.S. Pat. No. 5,848,994, for an invention entitled "IV Sets With Needleless/Spikeless Fittings And Valves", issued Dec. 15, 1998, which in turn claims priority from U.S. Pat. No. 5,645,538, filed on Mar. 12, 1996 for an invention entitled "Needleless Valve For Use In Intravenous Infusion", which in turn claims priority from U.S. Pat. No. 5,405,333 filed on Sep. 16, 1993 for an invention entitled "Liquid Medicament Bag With Needleless Connector Fitting Using Boat Assembly."

Additionally, this application claims priority from U.S. Pat. No. 5,735,826, for an invention entitled "Drip Chamber With Female Luer Fitting" issued Apr. 7, 1998, which in turn claimed priority from Ser. No. 08/377,514 for an invention entitled "Drip Chamber With Female Luer Fitting" filed Jan. 24, 1995, abandoned which in turn is a divisional application of issued U.S. Pat. No. 5,445,623, issued on Aug. 29, 1995 for an invention entitled "Drip Chamber With Luer Fitting". All are incorporated herein by reference.

FIELD OF THE INVENTION

The present invention relates generally to intravenous (IV) liquid medicament infusion equipment, and more particularly to drip chambers, valves and attachment mechanisms.

BACKGROUND OF THE INVENTION

One of the most widely used methods of medical therapy is the intravenous (IV) infusion of liquid medicaments and/or nutrients into the bloodstream of a patient. A familiar apparatus that is used in many IV infusion applications is an IV container, such as an IV bag or bottle, which contains the liquid to be infused into the patient.

When the IV container is a bag, or bottle, a rigid, hollow, sharpened IV spike is pushed into the container to establish a pathway for fluid communication through which the liquid can flow out of the container. The spike, in turn, is connected to or formed integrally with an inlet port of a small, elongated, transparent hollow container familiarly referred to as a "drip chamber", with the fluid pathway of the spike in fluid communication with the inlet port of the drip chamber.

Additionally, an IV line is connected to the bottom or proximal end of the drip chamber. Preferably, a means for controlling the flow (a roller clamp, pump, or other suitable flow regulating device) is engaged with the IV line, and a medical technician can manipulate the flow controlling means and thereby regulate fluid flow through the IV line. To complete the path for fluid communication from the IV container to the patient, a sharp needle is connected to the IV line to puncture the patient.

Usually, the container is elevated above the patient to establish a positive pressure head to force the fluid that is within the container through the drip chamber into the patient. Because the drip chamber is transparent, a medical technician can view the medicament as it passes (normally by dripping) through the drip chamber to aid the medical technician in establishing a predetermined flow rate of medicament into the patient as the medical technician adjusts the flow controlling means on the IV line.

While effective as aiding in the establishment of a predetermined fluid flow to the patient, existing drip chambers, as noted above, require the use of sharpened spikes to puncture the IV container containing the liquid. This is undesirable, particularly in the era of AIDS, because spikes, like other sharps instruments, can inadvertently puncture the bag or medical technician who is manipulating the spike and thereby potentially contaminate the bag contents or infect the technician with AIDS or other disease. Thus, as recognized by the present invention, it is desirable to avoid the use of sharp instruments whenever possible, while preserving the quick connection such instruments provide.

Further, it is desirable to connect and disconnect the drip chamber or other components in the IV system without spillage of medicament. As recognized by the present invention, such reduction in spillage can be obtained through the use of reflex valves which are compatible with spikeless drip chambers and other needleless IV components.

Accordingly, it is an object of the present invention to provide a valve apparatus in an IV drip chamber or other IV component for engaging a complementary fitting, without the need to use a sharp connector. Another object of the present invention is to allow connection and disconnection of components without the spillage of medicament. Yet another object of the present invention to provide a drip chamber which is easy to use and cost-effective to manufacture.

SUMMARY OF THE INVENTION

A drip chamber includes an elongated transparent container defining an elongated hollow chamber. The container has both a proximal end and a distal end. A cap covers the distal end of the container, and it includes a drip-forming tube, a cannula and an attachment element. The drip forming tube is disposed within the container while the cannula extends distally away from the tube and establishes a pathway for fluid communication between a IV medicament container and the drip chamber. The attachment element surrounds the cannula and is configured so as to removably engage the chamber with a connector.

In one presently preferred embodiment, the proximal end of the drip chamber is engageable with an IV tube and connector to establish a pathway for fluid communication between the drip chamber and a patient.

The cannula in the presently preferred embodiment, is metal, but the present invention recognizes that it may be formed from other materials such as plastic.

In another embodiment, the proximal end of the container is a solvent bondable port element in fluid communication with the chamber. In yet another embodiment, the proximal end of the container is also configurable as a luer fitting. The present invention recognizes that either a male or female luer fitting may be used in this embodiment.

On the distal side of the container, to retain the chamber with an IV medicament connector, an attachment element is used. In one embodiment, the attachment element is configured as a threaded collar fitting. In another embodiment, the attachment element is configured as a so called "A" clamp. The "A" clamp has an open and a normal retention configuration, and is biased to the normal configuration.

Preferably, the clamp includes two clamp elements, two fulcrum bars and two retaining lips. More clamp elements, fulcrum bars and lips are possible, but two of each is the most efficient. Specifically then, the clamp elements each have a distal pincer end and a proximal squeezeable end. The fulcrum bars are then attached on one side to the clamp element and on the opposite side to the cannula element or cannula holding element. The fulcrum bars are long enough such that the distal pincer ends are separated when the clamp is in the normal configuration. Ideally, the pincer ends open to facilitate easy assembly of the connector. The distal pincer ends may also configured with a lip to engage a complementary surface on the connector. The connector can be the port of any IV device, but the port of an IV bag, or other source of fluid, is preferable. To further facilitate engagement of the "A" clamp, the lips include an angular surface which, when urged against the connector port, move the pincer ends open sufficiently to allow mating of the lip and the complementary connector surface.

In another embodiment, a drip chamber includes an elongated container defining a hollow chamber. The chamber has both a proximal end and a distal end. A cap preferably covers the distal end of the container and it includes a drip forming tube, a valve body, at least one valve member disposed in the valve body and a valve actuating element. The drip forming tube is disposed within the container while the valve body defines a pathway for fluid communication through the cap. The valve member is disposed in the body and is biased to a first configuration where the path for fluid communication is not established. That is, in the first configuration, fluid may not pass through the body. Additionally, the valve member is movable to a second configuration where fluid communication through the body is permitted. Also disposed in the valve body is the valve actuating element. This element defines at least one engagement surface for contacting a mating element. Contact with the mating element causes the valve actuating element to move against the valve member. This pressure causes the valve member to move to the second configuration.

A variation of the above includes a valve member defining an outer periphery that is interrupted at least once within the periphery. The interruption within the periphery allows the fluid to pass directly through the member when in the second configuration rather than around the member (although the fluid could also pass through and around the member as envisioned above). In other words, when the valve member is in the second configuration, the interruption within the periphery defines an opening in the valve member allowing fluid through the valve member and thus, through the body.

The proximal end of the drip chamber may be configured in a variety of ways. In one embodiment the proximal end is configured as a male luer fitting. In another the proximal end is configured with a solvent bonded IV tube. And in yet another the proximal end is configured as a female luer fitting.

In another preferred embodiment, an IV component connector includes a valve body, a valve member and a valve element. In this embodiment, the valve body has a distal and a proximal end which define a path providing fluid communication through the body. The distal end has an attachment element to engage a complementarily shaped connector or surface. The proximal end has an outlet providing fluid communication with a connected component.

The valve member in this embodiment is disposed in the body and defines an outer periphery that is interrupted within the periphery at least once. The valve member is biased to a first configuration where the path for fluid communication is not established through the body. Also, the member is movable to a second configuration where fluid communication is permitted. The valve element is also disposed in the body and defines at least one engagement surface distally beyond the body. This surface contacts a mating element from another component that causes the valve element to move against the valve member thus moving the valve member to the second configuration.

In one presently preferred embodiment, the attachment element is configured as a male luer fitting to removably engage a female luer connector.

In another variation, the component connected to the proximal end may be any of various other IV components as disclosed in U.S. Pat. No. 5,645,538 to Richmond and incorporated herein by reference. Particular attention is directed to FIGS. 13, 15, 18, 19, 22–30; and the Specification, column 2, lines 14–18.

These and other aspects of the present invention can best be appreciated in reference to the accompanying drawings in which like numerals refer to like parts, and in which:

BRIEF DESCRIPTION OF THE DRAWINGS

FIG. 5 is a cross-sectional view of one embodiment of the IV component connector;

FIG. 6 is a cross-sectional view of another embodiment of the IV component connector;

FIG. 7 is a cross-sectional view of yet another embodiment of the IV component connector;

FIG. 8 is a cross-sectional view of the connector as shown in FIG. 5 combined with a drip chamber and a proximal end configured as a male luer fitting;

FIG. 9 is a cross-sectional view of the connector as shown in FIG. 6 combined with a drip chamber and a proximal end configured as a solvent bonded IV tube;

FIG. 10 is a cross-sectional view of the connector as shown in FIG. 7 combined with a drip chamber and a proximal end configured as a female luer fitting.

DETAILED DESCRIPTION OF THE PREFERRED EMBODIMENT

Figure 1:
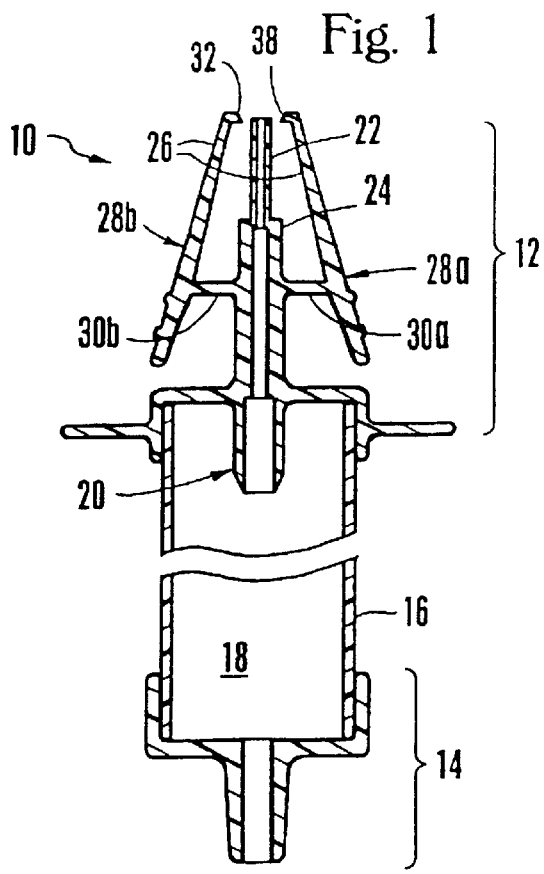
FIG. 1 is a cross-sectional view of a valve of the present invention showing a male cannula fitting drip chamber combined with an "A" clamp.

Referring initially to FIG. 1, the drip chamber with cannula of the present invention is shown and is generally designated as 10. Preferably, the drip chamber 10 is made of a plastic (e.g. polypropylene, polyethylene, etc.). As shown, the drip chamber 10 has a distal end 12 which can be engaged with a source of fluid, such as an IV container (not shown). It is to be understood that the source of fluid can be any container suitable for holding fluid medicaments, e.g., the source can be an IV bag, vial, IV bottle, semi-rigid container, syringe, etc.

Figure 2:
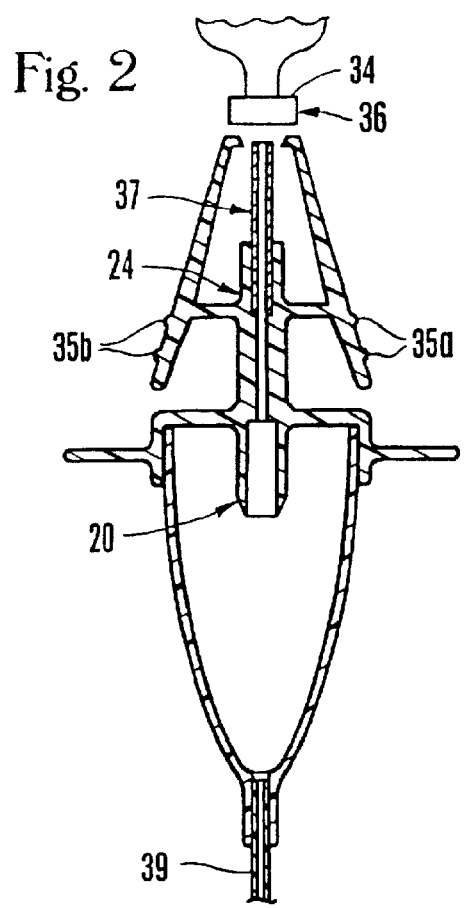
FIG. 2 is a cross-sectional view of an alternate inserted male cannula fitting drip chamber combined with an "A" clamp.

As further shown in FIG. 1, the drip chamber 10 has a proximal end 14 that can be engaged with an IV tube (shown as 39 in FIG. 2). Specifically, the IV tube 28 is advanced onto the proximal end 14 of the drip chamber 10 and is held on the proximal end 14 by solvent bonding, rf sealing, ultrasonic welding techniques, or other techniques known by those skilled in the arts.

Still referring to FIG. 1, the drip chamber 10 includes a hollow transparent glass or plastic container 16, and the container 16 defines a hollow chamber 18. As shown, the distal end 12 is configured as a cap including a drip forming tube 20, a cannula 22 formed integrally with a cannula holding element 24 and an attaching mechanism generally designated 26.

Cross referencing FIGS. 1 and 2, the attaching mechanism 26 is an "A" clamp. As shown, the "A" clamp consists of two clamp elements 28a, 28b. The clamp elements 28a, 28b are attached to the cannula holding element 24 by two fulcrum bars 30a, 30b. It can be noted now that the "A" clamp is biased to the retention configuration shown in the FIGS. The clamp elements 28a, 28b each have a lip 32 on the distal pincer end to engage a ledge 34 on the fluid source connector port 36. The lip 32 is configured with an angular surface 38 to facilitate engagement of the connector port 36. The distal end of the clamp elements 28a, 28b can have bumps 35a, 35b to improve the operator's grip while applying pressure to the clamp elements 28a, 28b. Squeezing pressure on the clamp elements 28a, 28b, below the fulcrum bars 30a, 30b, urges the clamp elements 28a, 28b, to an open configuration.

FIG. 2 shows an alternate embodiment which is identical to FIG. 1 in all essential respects, except that the cannula 42 is embedded into the cannula holding element 24. Additionally, FIG. 2 also shows the IV tube 39 inserted into the proximal end 14 of the drip chamber 10 and held in the proximal end 14 by solvent bonding, rf sealing, ultrasonic welding techniques, or other techniques known by those skilled in the arts.

Figure 3:
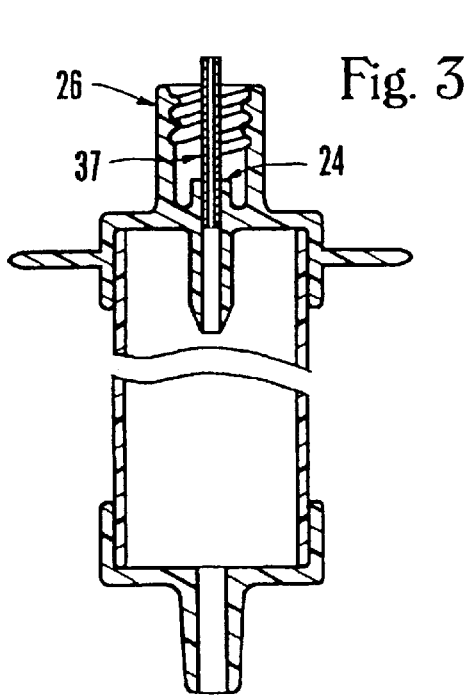
FIG. 3 is a cross-sectional view of a drip chamber with an embedded cannula fitting combined with a threaded collar fitting.

FIG. 3 shows an alternate embodiment which is identical in all essential respects to FIG. 2 except that the attaching mechanism 26 is alternately configured as a threaded collar surrounding the embedded cannula 37.

Figure 4:
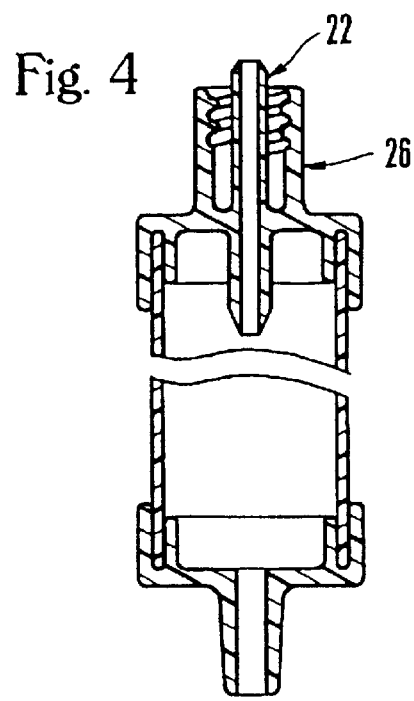
FIG. 4 is a cross-sectional view of a drip chamber with a cannula combined with a threaded collar fitting.

FIG. 4 shows an alternate embodiment which is identical in all essential respects to FIG. 1 except that the attachment mechanism 26 is configured as a threaded collar surrounding the integral cannula 22.

Now referring to FIG. 5, an IV component connector is shown and generally designated as 40. The connector 40 has a valve body 42 which has a distal end 44 and a proximal end 46. The body defines a fluid passageway 48 which provides a pathway for fluid communication through the body 42. As can be readily observed in FIG. 5, the distal end 44 is configured as a male fitting for connection to a corresponding female fitting (not shown). Fluid communication through the body 42 ends at the proximal end 46 where an outlet 50 is provided. The proximal end 46 attaches to various other IV components as disclosed in issued U.S. Pat. No. 5,645,538 to Richmond and incorporated herein by reference.

Still referring to FIG. 5, a valve member 52 is shown disposed in the body 42 to selectively block the fluid passageway 48. The valve member 52 is preferably made from plastic, rubber, etc., and defines an outer periphery that may be interrupted by a fluid orifice 56. Those skilled in the art will recognize that more than one fluid orifice 56 is possible and that the orifice 56 may be shaped in a variety of ways. When the valve is in place in a closed configuration, the orifice 56 is sealed and consequentially, a fluid tight seal between the valve member 52 and the interior surface of the body 42 is established. It is to be understood that the valve member 52 is biased to the closed configuration as shown in FIG. 5, wherein no fluid communication is permitted through the valve body 42 (and hence through the outlet 50). On the other hand, when pressure is exerted on the member 52 from the distal side 44 of the valve member 52, the member 52 is moved to cause the fluid orifice 56 to open and, thus, to move the member 52 to the open configuration.

FIG. 5 additionally shows that a valve element 60 is reciprocably disposed in the fluid passageway 48. The valve element 60 is formed with a lower probe 62, a retention element 63 and an upper contact flange 64. When the valve element 60 is urged into the valve body 42, the lower probe 62 exerts pressure, thus opening the valve member 52 as discussed above. As shown, the retention element 63 retains the valve element 60 in the valve body 42 by contacting a surface 66.

It can now be understood that the distal end 44, configured as a male Luer fitting, can be engaged with a complementarily shaped female Luer fitting (not shown). This engagement causes the upper contact flange 64 of the valve element 60 to be contacted by the female Luer fitting (not shown) and to urge the valve element 60 into the valve body 42. When the valve element 60 is urged sufficiently, it contacts the valve member 52 and urges the valve member 52 to the open configuration, thereby allowing fluid communication through the orifice 56, and hence through the fluid passageway 48.

Now referring to FIG. 6, an alternate embodiment of the IV component connector is shown. This is in all essential respects identical to FIG. 5, except that the valve element 60 has a skirt 65 for urging the valve member 52 downwardly and further urging the fluid orifice 56 to the open configuration. Also, as can best be seen in FIG. 6, the valve member 52 need not be rigidly attached to the valve body 42.

FIG. 7 shows yet another alternative embodiment of the IV component connector of the present invention. This is in all essential respects identical to FIG. 5, except that the valve member 52 can also be held in place by trapping between the separate sub-components of the valve body 42. This Figure also best illustrates an alternate valve member 52. In this embodiment, the distal side of the valve member 52 is essentially flat while the proximal side bulges in the center. Said another way, the thickness of the valve member 52 increases towards the center. Importantly, because of the thickening of the valve member 52 towards the center on the proximal side of the valve member 52, pressure from the proximal side 46 of the valve member 52 will cause the valve member 52 to close more tightly. That is, backflow pressure will act to close the valve member 52 and increased pressure will more tightly close the valve 52.

FIGS. 8, 9 and 10 show the various embodiments of the component connector of the present invention in combination with drip chambers. FIG. 8 also shows the proximal end configured as a male luer fitting 70. The male luer fitting 70 can then be connected and disconnected from a corresponding female fitting 72. FIG. 9 shows the proximal end configured as a solvent bonded IV tube 74. FIG. 10 shows the proximal end configured as a female luer fitting 76. The female luer fitting 76 can then be connected and disconnected from a corresponding male fitting 78.

Figure 11:
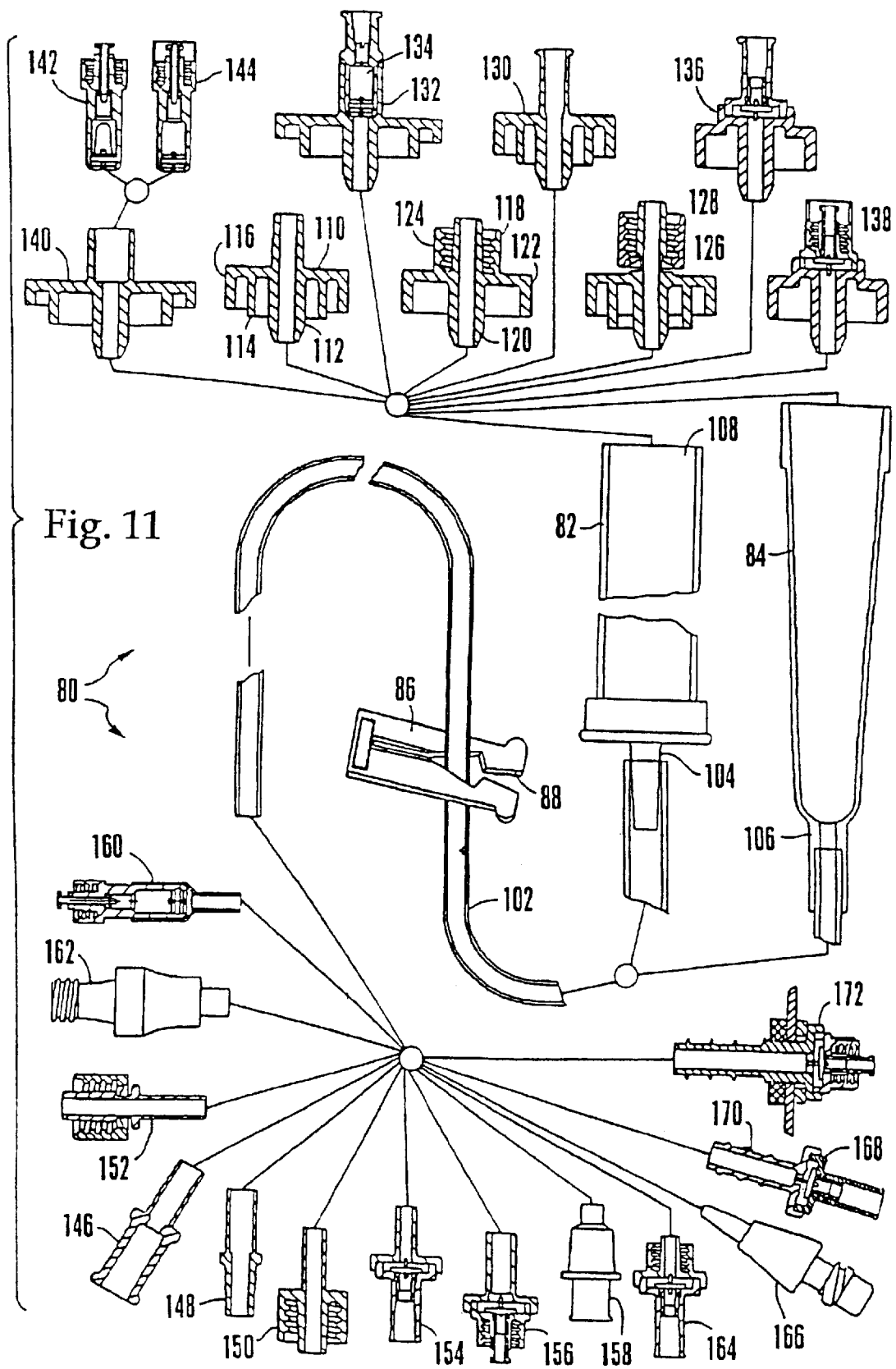
FIG. 11 is a partial cross-sectional view of an IV set of the present invention, showing various drip chamber upper connections and various drip chamber lower connections in exploded relationships.

Now referring to FIG. 11, an IV set is shown, generally designated 80. As can be appreciated in reference to FIG. 11, the present IV set includes a drip chamber, an upper needleless connector on the top of the drip chamber to connect the top to a needleless fitting (such as any of those shown herein), an IV tube connected to the bottom of the drip chamber, a flow restrictor engaged with the IV tube, and a lower needleless connector connected to the end of the IV tube to connect the tube to a needleless fitting (such as any of those shown herein).

As shown in FIG. 11, the drip chamber can be an elongated hollow transparent plastic cylindrical drip chamber 82 or tapered drip chamber 84. In any case, the present drip chamber is "elongated" in that its length is at least half again as great as its diameter. The IV tube is a hollow plastic IV tube known in the art, with the flow restrictor being an open slide clamp 86 having an open head end 88 (FIG. 11).

In the particular embodiment shown in FIG. 11, an IV tube 102 can be connected by attaching the tube 102 by means well-known known in the art to an exit port 104 of the cylindrical drip chamber 82 or to and exit port 106 of the tapered drip chamber 84. For succinctness of disclosure, the discussion below will focus on the cylindrical drip chamber 82, but it is to be understood that the discussion below is equally relevant to the tapered drip chamber 84 or indeed any well-known drip chamber. The open clamp 86 can be manipulated by means well-known in the art to constrict the IV tube 102 to stop fluid flow therethrough.

Figure 12:
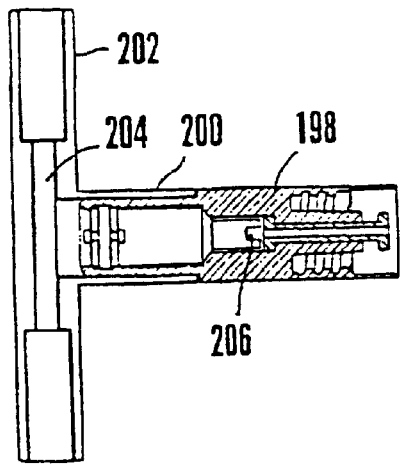
FIG. 12 is a cross-sectional view of a male reflux valve bonded to a "T"-site connector.

FIG. 12 shows a male member valve 208 which is disposed in a port 210 of a so-called "T"-site connector 202. The T-site connector 202 defines a main fluid passageway 204 and a secondary fluid passageway 206, and the male valve 198 can be manipulated as described above to selectively permit fluid communication through the secondary fluid passageway 206 of the T-site connector.

Figure 13:
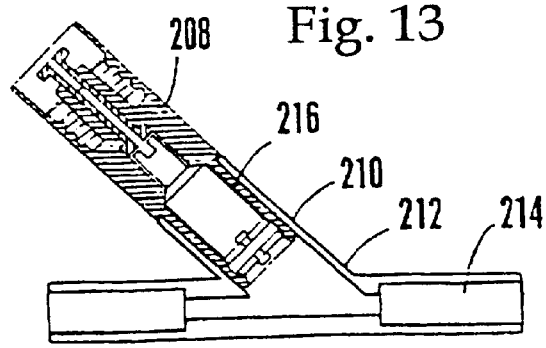
FIG. 13 is a cross-sectional view of a male reflux valve bonded to a "Y"-site connector.

FIG. 13 shows a male member valve 208 which is disposed in a port 210 of a so-called "Y"-site connector 212. As shown, the Y-site connector 212 defines a main cylindrical fluid passageway 214 and a secondary fluid passageway 216. The valve 208 can be operated as disclosed above to selectively block fluid communication through the secondary passageway 216 of the Y-site connector 212.

Figure 14:
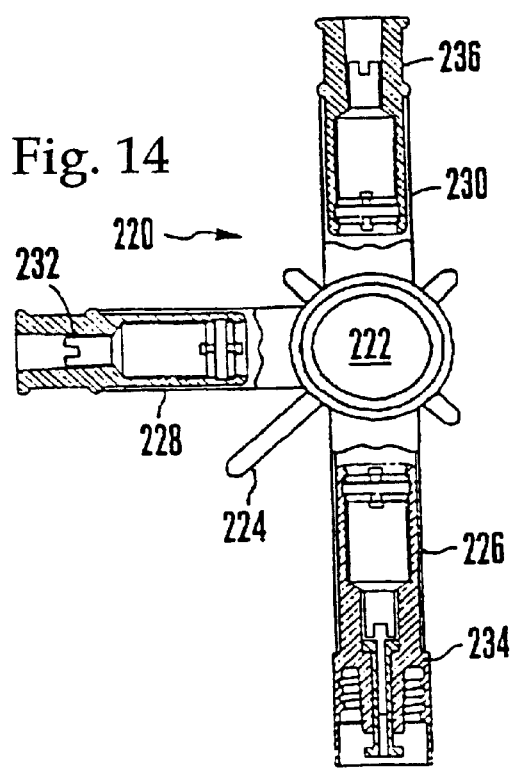
FIG. 14 is a plan cross-sectional view of a plurality of reflux valves operably engaged with a stopcock.

FIG. 14 shows an IV stopcock, generally designated 220. In accordance with principles well known in the art, the stopcock 220 includes a central fluid passageway that is covered by a cover plate 222, and an operating hand wheel 224. Additionally, the stopcock 220 can include at least two ports, and can include additional ports.

Figure 15:
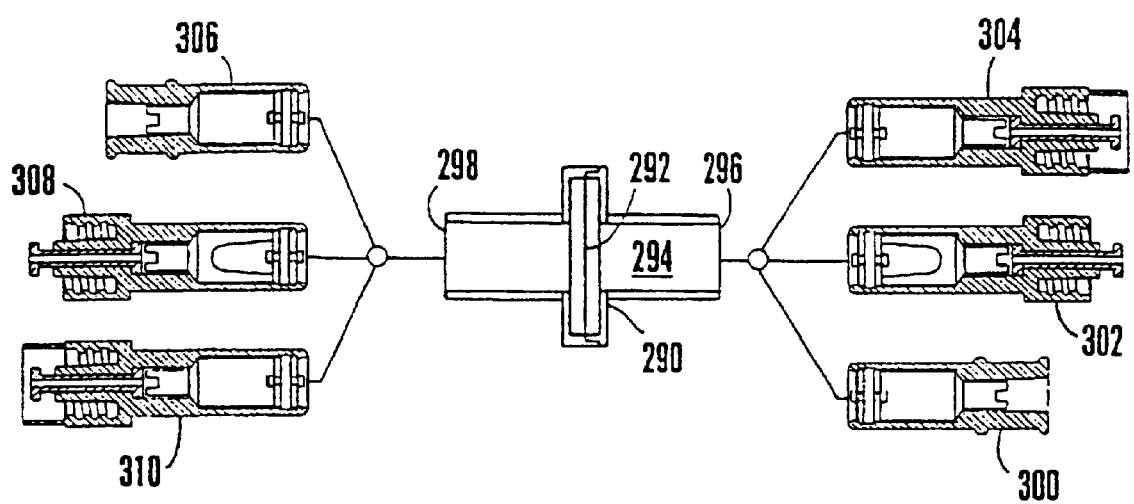
FIG. 15 is an exploded cross-sectional view of various reflux valves in combination with a filter assembly.

As shown in FIG. 15, the IV component can be a tubular IV connector 290 having a filter 292 disposed athwart a fluid passageway 294 defined by the connector 290. The connector 290 has an inlet port 296 and an outlet port 298. The inlet port 296 can be selectively blocked by engaging the port 296 with any one of a female member valve 300, a first male member valve 302, or a second male member valve 304. Similarly, the outlet port 298 can be selectively blocked by engaging the port 298 with any one of a female member valve 306, a first male member valve 308, or a second male member valve 310. Accordingly, the IV component shown in FIG. 15 is resealable, in that upon disconnecting a fitting from the valve member in one of the ports 296, 298, fluid flow through the component is prevented by the valve member in the disconnected port.

Figure 16:
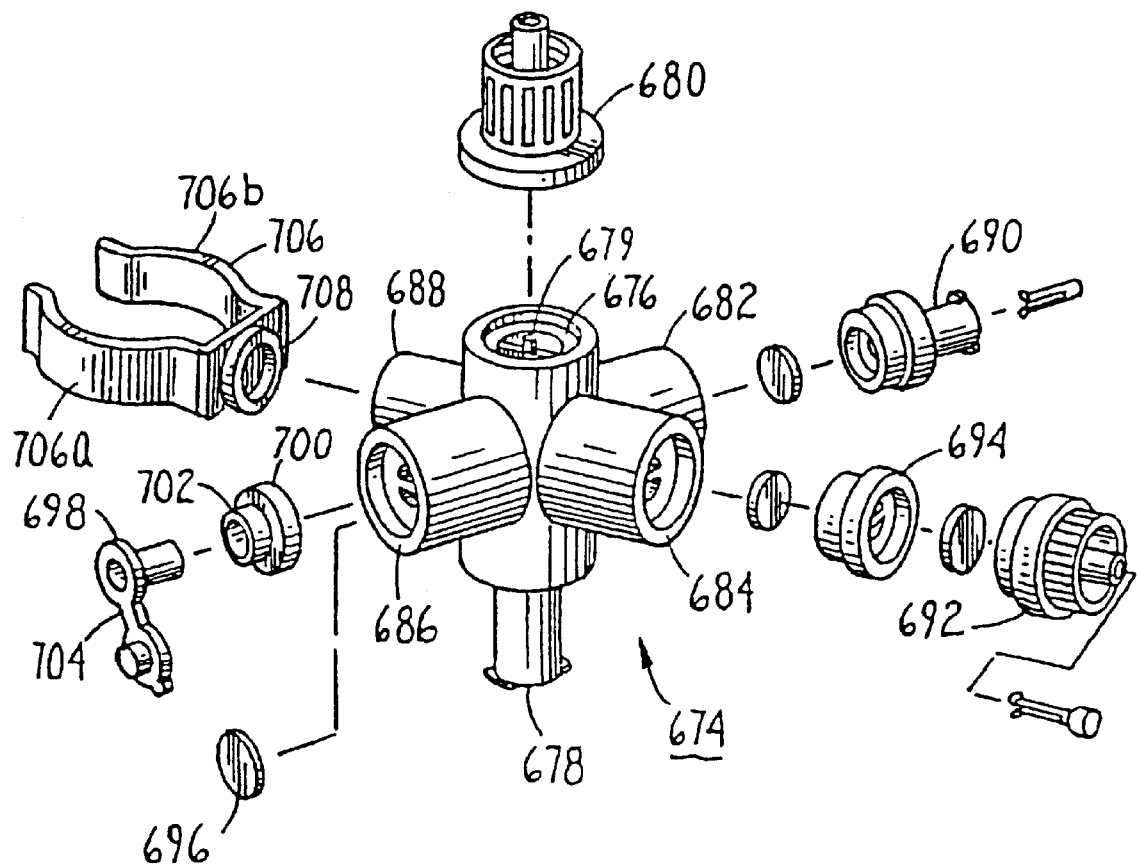
FIG. 16 is an exploded isometric view of a four-way valve with various associated components including Luer flags with reflux valves.

Now referring to FIG. 16, a novel multiport IV valve of the present invention, generally designated 674, can be seen. As shown, the multiport valve 674 includes a first port 676 which is generally cylindrically shaped, and a second port 678 which is also generally cylindrically shaped and is configured as a female Luer fitting. As can be appreciated in reference to FIG. 16, the first and second ports 676, 678 are coaxial and establish a main fluid passageway therebetween. A first male Luer valve 680 is fixedly engaged with the first port 676 for selectively blocking fluid communication therethrough.

FIG. 16 additionally shows that the multiport valve 674 includes third, fourth, fifth and sixth ports 682, 684, 686, 688, all of which are generally cylindrically shaped. As shown, the third and fifth ports 682, 686 are coaxial with each other. Likewise, the fourth and sixth ports 684, 688 are coaxial with each other. Each of the third through sixth ports 682, 684, 686, 688 defines a respective fluid pathway, and fluid communication through the fluid pathway can be selectively established or otherwise effected as disclosed below.

For example, a female reflux valve 690 can be disposed in the third fluid port 682 for selectively establishing fluid communication through the port 682 and into the main fluid passageway 679 in accordance with principles disclosed previously. Moreover, a combination male reflux valve-check valve 692, 694, can be disposed in the fourth fluid inlet port 684 of the multiport valve 674. If desired, the male reflux valve 692 can be replaced with a female reflux valve (not shown) which is substantially identical to the female reflux valve 30 shown in FIG. 1.

Additionally, fluid communication through the fifth inlet port 686 can be permanently blocked if desired by bonding a plug 696 within the port 686 by means well known in the art. Alternatively, the fifth fluid inlet port 686 can hold a fluid filter, e.g. a filter 698. As shown, the falter 698 includes a filter element 700 having a membrane 702 through which air can pass. The filter 698 also includes a plug element 704 which engages filter element 700 and which holds the filter element 700 within the sixth fluid port 686.

While the particular drip chamber with valve as herein shown and described in detail is fully capable of attaining the objects stated above, it is to be understood that it is but the presently preferred embodiments of the present invention, and that the scope of the present invention is accordingly to be limited by nothing other than the appended claims where singular nouns do not mean "one and only one," but rather, "at least one" unless otherwise specifically noted as "one and only one."

I claim:

1. A valve comprising:
    a valve body configured as a male luer fitting, the valve body having a distal end and a proximal end, the body defining a path providing fluid communication through the body, the distal end having an attachment element to engage a component;
    a valve member disposed in the body, defining an outer periphery that is interrupted at least once within the periphery and biased to a first configuration wherein the path for fluid communication is not established through the body, the member being moveable to a second configuration, wherein fluid communication through the body is permitted; and an activating feature to move the valve member to the second configurations.

2. A valve as recited in claim 1 wherein the activating feature further defines a retaining element for contacting a surface in the valve body.

3. A valve as recited in claim 1 wherein the activating feature further defines at least one engagement feature for contacting a mating element to cause the activating feature to move the valve to the second configuration.

4. A valve as recited in claim 1 wherein the valve member reseals when disconnected.

5. A valve as recited in claim 1 in combination with a syringe.

6. A valve as recited in claim 1 in combination with an IV container.

7. A valve as recited in claim 1 in combination with a Y-site or a T-site.

8. A valve as recited in claim 1 in combination with a multiport-valve.

9. A valve as recited in claim 7 in combination with a filter.

10. A valve as recited in claim 7 in combination with a hanger.

11. A valve as recited in claim 1 in combination with a belly-button port.

12. A valve as recited in claim 1 in combination with a spike and/or IV container.

13. A valve as recited in claim 11 in combination with a container.

14. A valve as recited in claim 11 in combination with a spiker.

15. A valve as recited in claim 11 in combination with a check valve.

16. A valve as recited in claim 11 in combination with a drip chamber, wherein the drip chamber comprises:
    a) an elongated transparent container defining an elongated hollow chamber, the container having an open proximal end and a distal end; and
    b) a cap covering the distal end of the container, the cap including:
        i) a drip-forming tube disposed within the a container;
        ii) a valve body defining a pathway for fluid communication through the cap;
        iii) at least one valve member disposed in the body and biased to a first configuration wherein the path for fluid communication is not established through the body, the member being movable to a second configuration, wherein fluid communication through the body is permitted; and
        iv) an actuating element to move the valve member to the second configuration.

17. A valve as recited in claim 16 wherein the activating element further defines a retaining element for contacting a surface in the valve body.

18. A valve as recited in claim 16 wherein the activating feature further defines at least one engagement feature for contacting a mating element to cause the activating feature to move the valve to the second configuration.

19. A valve as recited in claim 16 wherein the valve member defines an outer periphery that is interrupted at least once within the periphery.

20. A valve as recited in claim 16 wherein the proximal end is configured as a male luer fitting.

21. A valve as recited in claim 16 wherein the proximal end is configured as a port for IV tubing.

22. A valve as recited in claim 16 wherein the proximal end is configured as a female luer.

23. A valve as recited in claim 16 wherein the valve member reseals when disconnected.

24. A valve as recited in claim 16 wherein the valve member reseals when disconnected .

25. A valve as recited in claim 16 in combination with a set.

26. A valve as recited in claim 1 wherein the valve component is configured as a connector comprising:
    a) a valve body having a distal end and a proximal end, the body defining a path providing fluid communication through the body, the distal end having an attachment element to engage a component;
    b) at least one valve member disposed in the body, defining an outer periphery that is interrupted at least once within the periphery and biased to a first configuration wherein the path for fluid communication is not established through the body, the member being moveable to a second configuration, wherein fluid communication through the body is permitted; and
    c) an actuating element to move the valve member to the second configuration.

27. A valve as recited in claim 26 wherein the valve actuating element further defines a retaining element for contacting a surface in the valve body.

28. A valve as recited in claim 26 wherein the activating feature further defines at least one engagement feature for contacting a mating element to cause the activating feature to move the valve to the second configuration.

29. A valve as recited in claim 26 wherein the attachment element is a male luer fitting.

30. A valve as recited in claim 26 wherein the component is a component selected from the group consisting of: IV containers, bags, spikes, syringes, IV sets, drip chambers, filters, Burette chambers, stopcocks, multiport valves, belly button port, and connector fittings.

31. A valve as recited in claim 1 wherein the valve body is configured as a male connector, the valve body having a distal end and a proximal end, the body defining a path providing fluid communication through the body, a valve member disposed in the body; and an activating feature to move the valve member to the second configuration.

32. A valve as recited in claim 31 wherein the activating feature further defines a retaining element for contacting a surface in the valve body.

33. A valve as recited in claim 31 a wherein the activating feature further defines at least one engagement feature for contacting a mating element to cause the activating feature to move the valve to the second configuration.

34. A valve as recited in claim 31 wherein the valve member reseals when disconnected.

35. A valve as recited in claim 31 in combination with a syringe, an IV container, fluid lines, sets, drip chambers, Burette chambers, stopcocks, vials, a Y-site or a T-site, a multiport-valve, a filter, a hanger, a belly-button port, a port, a spike and/or IV container, a container, a spike, and a check valve.

* * * * *